(12) United States Patent
Lin (10) Patent No.: US 10,010,269 B2
(45) Date of Patent: Jul. 3, 2018

(54) CALIBRATION METHOD AND ELECTRONIC DEVICE

(71) Applicant: Wistron Corporation, New Taipei (TW)

(72) Inventor: Zhao-Yuan Lin, New Taipei (TW)

(73) Assignee: Wistron Corporation, New Taipei (TW)

( * ) Notice: Subject to any disclaimer, the term of this patent is extended or adjusted under 35 U.S.C. 154(b) by 330 days.

(21) Appl. No.: 14/951,495

(22) Filed: Nov. 25, 2015

(65) Prior Publication Data

US 2017/0036088 A1    Feb. 9, 2017

(30) Foreign Application Priority Data

Aug. 5, 2015 (TW) .............................. 104125363 A (51) Int. Cl.
*A61B 5/11* (2006.01)
*A63B 69/36* (2006.01)

(52) U.S. Cl.
CPC ...................................... *A61B 5/11* (2013.01)

(58) Field of Classification Search
CPC . A63B 69/36; A63B 24/0006; A63B 24/0021; A63B 2024/0009; A63B 2024/0015; A63B 2024/0028; A63B 39/3632; A61B 5/11; A61B 5/103; G01P 15/00; G01P 21/00
See application file for complete search history.

(56) References Cited

FOREIGN PATENT DOCUMENTS

CN            102023700 B        6/2012

OTHER PUBLICATIONS

Cao Nguyen Khoa Nam et al., Golf Swing Motion Tracking Using Inertial Sensors and a Stereo Camera, Apr. 2014, IEEE Transactions on Instrumentation and Measurement, vol. 63, No. 4, pp. 943-952.*

* cited by examiner

*Primary Examiner* — Toan Le
(74) *Attorney, Agent, or Firm* — Winston Hsu (57) ABSTRACT

A calibration method for calibrating a simulated motion trace is disclosed. The calibration method includes measuring an acceleration, an inclination angle and an azimuth of a terminal of a sports equipment, computing the simulated motion trace of the terminal according to the acceleration, the inclination angle and the azimuth, estimating a trace surface on which the simulated motion trace locates according to the simulated motion trace, computing a rotational angle between the trace surface and a display surface, projecting the simulated motion trace onto the display surface according to the rotational angle to generate a calibrated trace, and displaying the calibrated trace.

14 Claims, 8 Drawing Sheets

CALIBRATION METHOD AND ELECTRONIC DEVICE

BACKGROUND OF THE INVENTION

1. Field of the Invention

The present invention relates to a calibration method and electronic device, and more particularly, to a calibration method and electronic device calibrating a simulated motion trace by vector transformation.

2. Description of the Prior Art

With advances of micro electro mechanical systems (MEMS), accelerometers or G-sensors are embedded in various sports equipments to record usage data of athletes, which can be utilized for analyzing athletic skills. For example, a baseball bat or a golf club is embedded with an accelerometer to record data of a bat swing or a club swing, which is further analyzed and simulated by a computer and displayed on a screen. As a result, the athletes can repeatedly watch the bat swing or club swing to improve athletic skills.

Figure 1A:
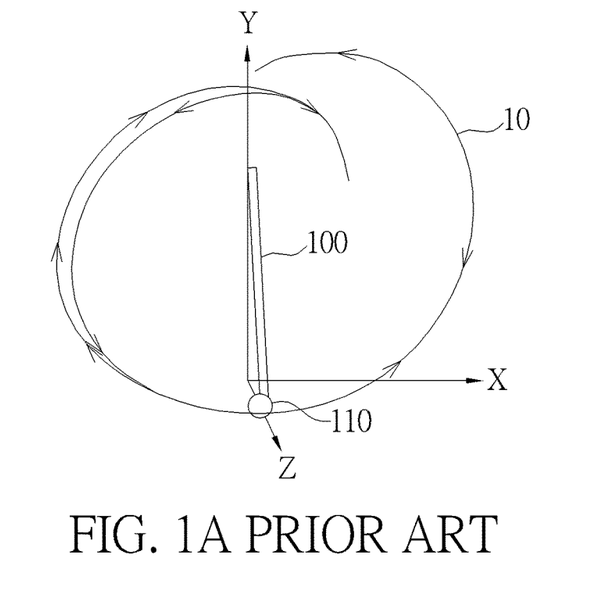
FIG. 1A is a schematic diagram of a simulated golf swing trace of the prior art.
Figure 1B:
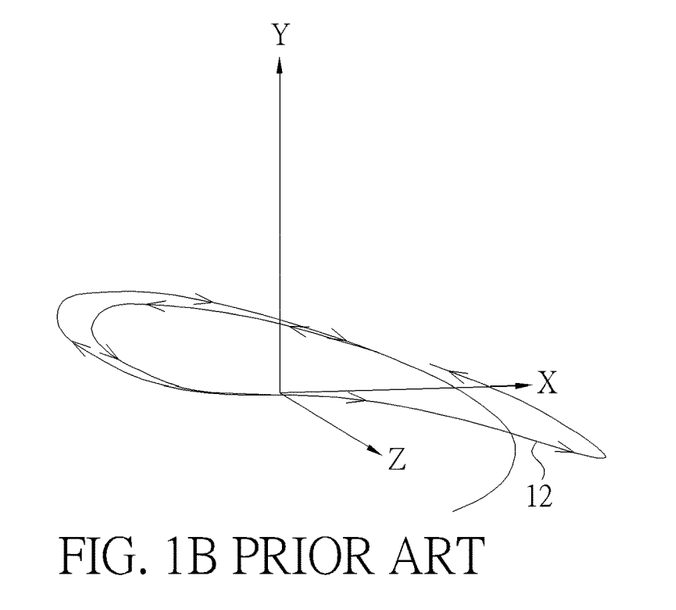
FIG. 1B is a schematic diagram of another simulated golf swing trace of the prior art.

Please refer to FIG. 1A, which is a schematic diagram of a simulated golf swing trace 10 of the prior art. In order to simulate the golf swing trace 10, acceleration data recorded by an accelerometer embedded in a head 110 of a golf club 100 are required. In addition to the acceleration data, inclination angle data recorded by the accelerometer are also required to correctly simulate the golf swing trace 10. If the inclination angle data are incorrect, a simulated golf swing trace 12 will be rotated as illustrated FIG. 1B, and is difficult for watch.

Figure 1C:
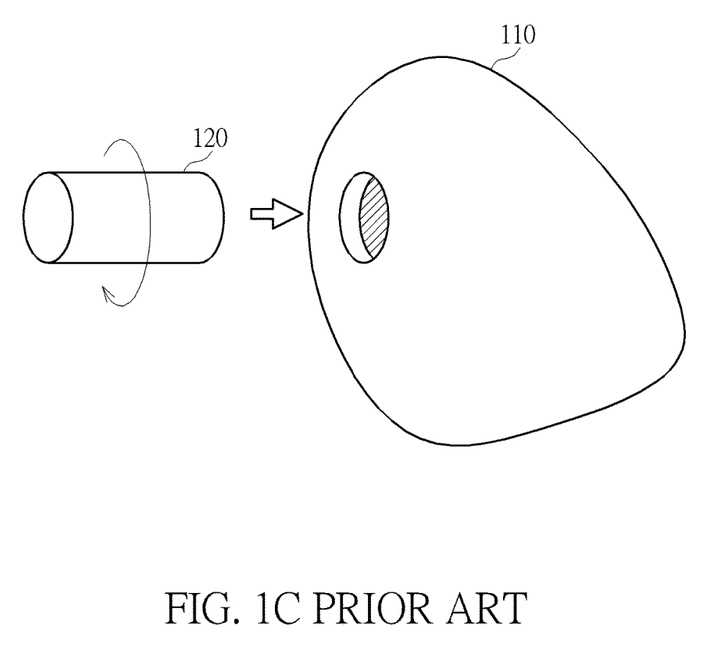
FIG. 1C is a schematic diagram of an accelerometer and a gulf club head of the prior art.

In fact, the inclination angle data relate to an installation angle of the accelerometer in the head 110, as illustrated in FIG. 1C. In FIG. 1C, an accelerometer 120 is screwed into the head 110 and then fixed by a thread or adhesive. However, due to technical limitation, a manufacturer cannot guarantee that the accelerometer 120 is installed in the same position for each sports equipment, such that the recorded inclination angle is biased.

Therefore, before delivery to retail stores, the manufacturer has to calibrate the position of accelerometer 120 for each sports equipment to minimize the inclination angle error. In addition to the initial calibration, the accelerometer 120 will loose and drift from the initial installation position after intense club swing, and therefore has to be regularly calibrated, which is troublesome to both of the manufacturer and the user.

Accordingly, the industry focuses on reducing the interference caused by the positional error of the accelerometer for motion trace simulation.

SUMMARY OF THE INVENTION

It is therefore an objective of the present invention to provide a calibration method and electronic device to reduce interference caused by the positional error of the accelerometer for motion trace simulation.

The present invention discloses a calibration method for calibrating a simulated motion trace of a sports equipment, the calibration method comprising measuring an acceleration, an inclination angle and an azimuth of a terminal of the sports equipment; computing the simulated motion trace of the terminal according to the acceleration, the inclination angle and the azimuth; estimating a trace surface on which the simulated motion trace locates according to the simulated motion trace; computing a rotational angle between the trace surface and a display surface; projecting the simulated motion trace onto the display surface according to the rotational angle to generate a calibrated trace; and displaying the calibrated trace.

The present invention further discloses an electronic device for calibrating a simulated motion trace, the electronic device comprising a receiving unit, for receiving an acceleration, an inclination angle and an azimuth of a motion; a processing means; a storage unit, for storing a program code to indicate the processing means to perform the following steps computing the simulated motion trace of the motion according to the acceleration, the inclination angle and the azimuth; estimating a trace surface on which the simulated motion trace locates according to the simulated motion trace; computing a rotational angle between the trace surface and a display surface; and projecting the simulated motion trace onto the display surface according to the rotational angle to generate a calibrated trace; and a display unit, for displaying the calibrated trace.

These and other objectives of the present invention will no doubt become obvious to those of ordinary skill in the art after reading the following detailed description of the preferred embodiment that is illustrated in the various figures and drawings.

DETAILED DESCRIPTION

Figure 2:
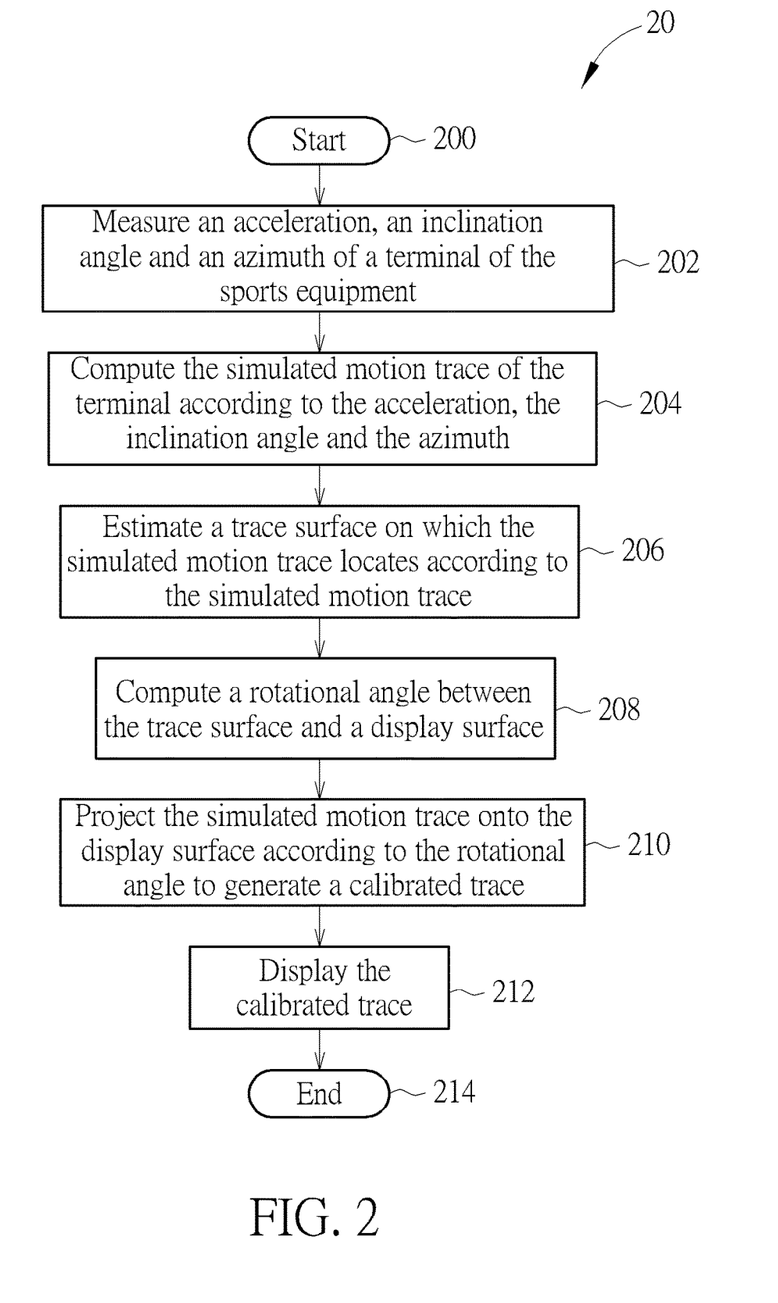
FIG. 2 is a flowchart of a calibration process according to an embodiment of the present invention.

Please refer to FIG. 2, which is a flowchart of a calibration process 20 according to an embodiment of the present invention. The calibration process 20 is utilized for calibrating a simulated motion trace of a sports equipment, and includes the following steps:

Step 200: Start.

Step 202: Measure an acceleration, an inclination angle and an azimuth of a terminal of the sports equipment.

Step 204: Compute the simulated motion trace of the terminal according to the acceleration, the inclination angle and the azimuth.

Step 206: Estimate a trace surface on which the simulated motion trace locates according to the simulated motion trace.

Step 208: Compute a rotational angle between the trace surface and a display surface.

Step 210: Project the simulated motion trace onto the display surface according to the rotational angle to generate a calibrated trace.

Step 212: Display the calibrated trace.

Step 214: End.

In short, in order to solve the problem of the rotational simulated motion trace 12 caused by the inclination angle error, the calibration process 20 presumes that an error exists in the measured inclination angle, simulates the motion trace according to the erroneous inclination angle, and estimate the trace surface of the simulated motion trace. As long as the trace surface is determined, the simulated motion trace locating on the trace surface can be projected onto the display surface by vector transformation. As a result, the display problem caused by the inclination angle error can be eliminated.

Figure 3:
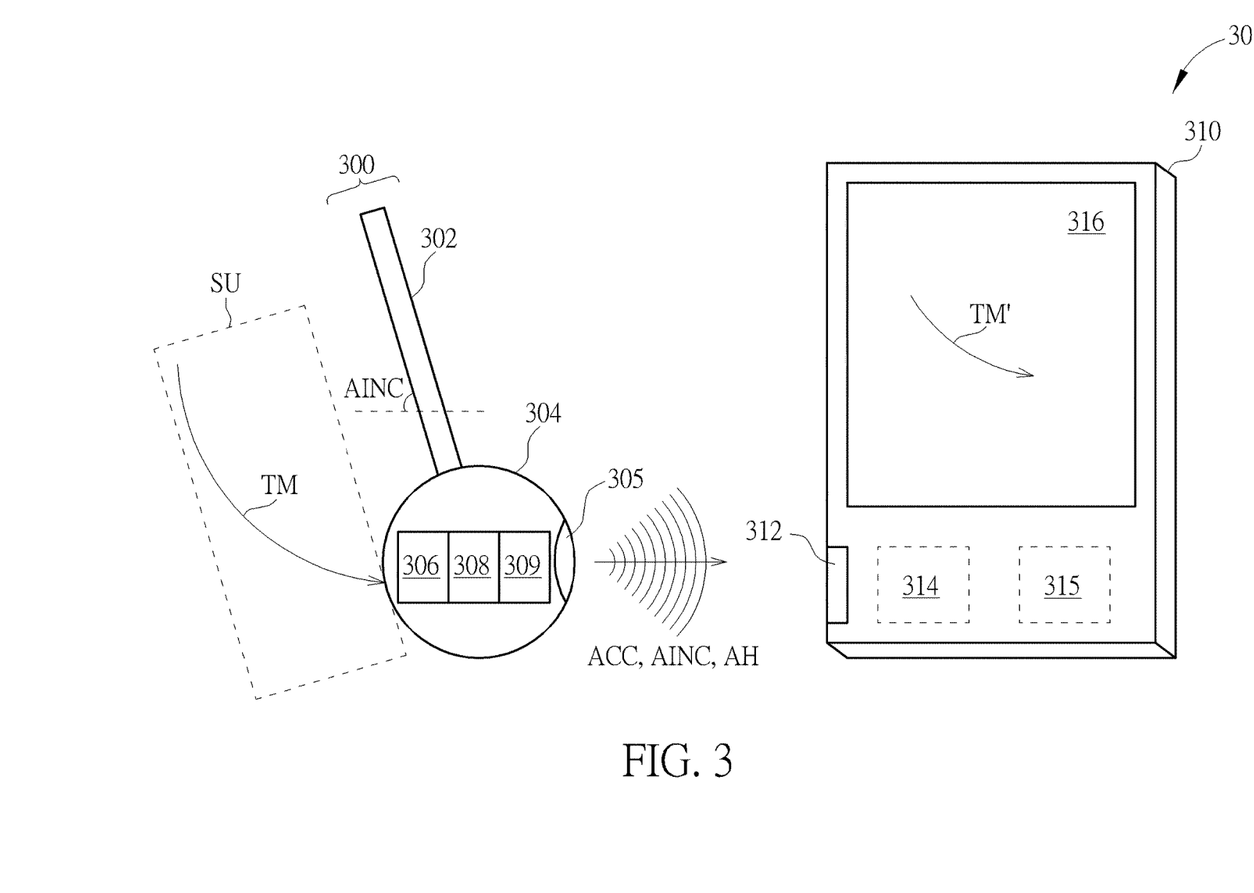
FIG. 3 is a schematic diagram of a calibration system according to an embodiment of the present invention.

For more implementation details in regard to the calibration process 20, please refer to FIG. 3, which is a schematic diagram of a calibration system 30 according to an embodiment of the present invention. The calibration system 30 is utilized for performing the calibration process 20, and includes a sports equipment 300 and an electronic device 310. The sports equipment 300 includes a stick 302 and a head 304. The head 304 is installed at one end of the stick 302, and includes a first accelerometer 306, a second accelerometer 308, a gyro meter 309 and an interface unit 305. The first accelerometer 306 is utilized for measuring an acceleration ACC of the head 304. The second accelerometer 308 is utilized for measuring an inclination angle AINC of the head 304. The gyro meter 309 is utilized for measuring an azimuth AH of the head 304. The interface unit 305, such as a bluetooth or Wi-Fi module, is utilized for transmitting data of the acceleration ACC, the inclination angle AINC and the azimuth AH to the electronic device 310. The electronic device 310, such as a smart phone or personal computer, includes a receiving unit 312, a processing means 314, a storage unit 315 and a display unit 316. The receiving unit 312 is utilized for receiving the data of the acceleration ACC, the inclination angle AINC and the azimuth AH transmitted by the interface unit 305. The storage unit 315 is utilized for storing a program code to indicate the processing means 314 to perform the Steps 206-210. That is, the processing means 314 computes a simulated motion trace TM of the head 304 according to the acceleration ACC, the inclination angle AINC and the azimuth AH, and estimates a trace surface SU on which the simulated motion trace TM locates. Next, the processing means 314 computes a rotational angle AR between the trace surface SU and a default display surface SD, and projects the simulated motion trace TM onto the display surface SD according to the rotational angle AR to generate a calibrated trace TM'. Finally, the display unit 116 displays the calibrated trace TM'. As a result, a user can improve athletic skills based on the calibrated trace TM'.

Figure 4A:
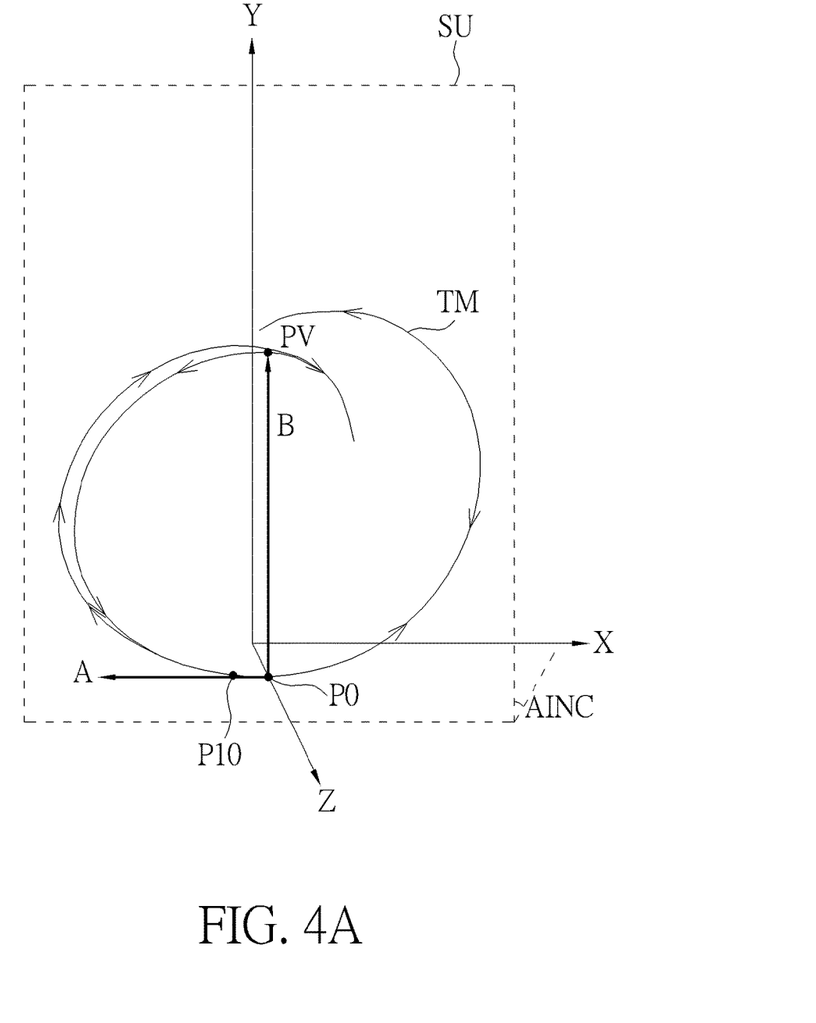
FIGS. 4A-4D are schematic diagrams of trace surfaces according to embodiments of the present invention.

To further illustrate the relationship among the simulated motion trace TM, the trace surface SU, the inclination angle AINC, the rotational angle AR and the calibrated trace TM', please refer to FIGS. 4A-4D. Note that, the inclination angle AINC refers to an angle between the head 304 and a horizontal plane. Since the trace surface SU is determined based on the simulated motion trace TM of the head 304, the inclination angle AINC also refers to an angle between the trace surface SU and the horizontal plane as illustrated in FIG. 4A. According to Kinematics and Geometry, as long as the acceleration ACC, the inclination angle AINC and the azimuth AH is acquired, the processing means 314 can accordingly reconstruct the simulated motion trace TM as shown in FIG. 4A. Note that, the simulated motion trace TM of FIG. 4A is reconstructed when an error of the inclination angle AINC is insignificant. In fact, if the error of the inclination angle AINC is significant, the simulated motion trace TM will become flat as shown in FIG. 3C. However, regardless of the insignificant error (FIG. 4A) or the significant error (FIG. 4C), the simulated motion trace TM can be projected onto a preferable surface, such as the X-Y plane shown in FIGS. 4A and 4C. The X-Y plane is parallel to the user, such that the user can clearly examine the calibrated trace TM'.

In FIG. 4A, preferably, the processing means 314 can choose an acceleration ACC0 of an initial point P0 of the head 304 to be an axis vector A of the trace surface SU, and search another point PV from the simulated motion trace TM, such that an inner product of a vector (P0→PV) and the axis vector A is zero. In such a situation, the processing unit 314 can determine the vector (P0→PV) to be the other axis vector B of the trace surface SU. As long as the axis vectors A, B are chosen, the trace surface SU is determined. However, the trace surface SU may not be the most preferable aspect for watch. That is, the processing means 314 can further project the simulated motion trace TM from the trace surface SU to the display surface SD, such as the X-Y plane of FIG. 4B, to form the calibrated trace TM' on the X-Y plane.

Figure 4B:
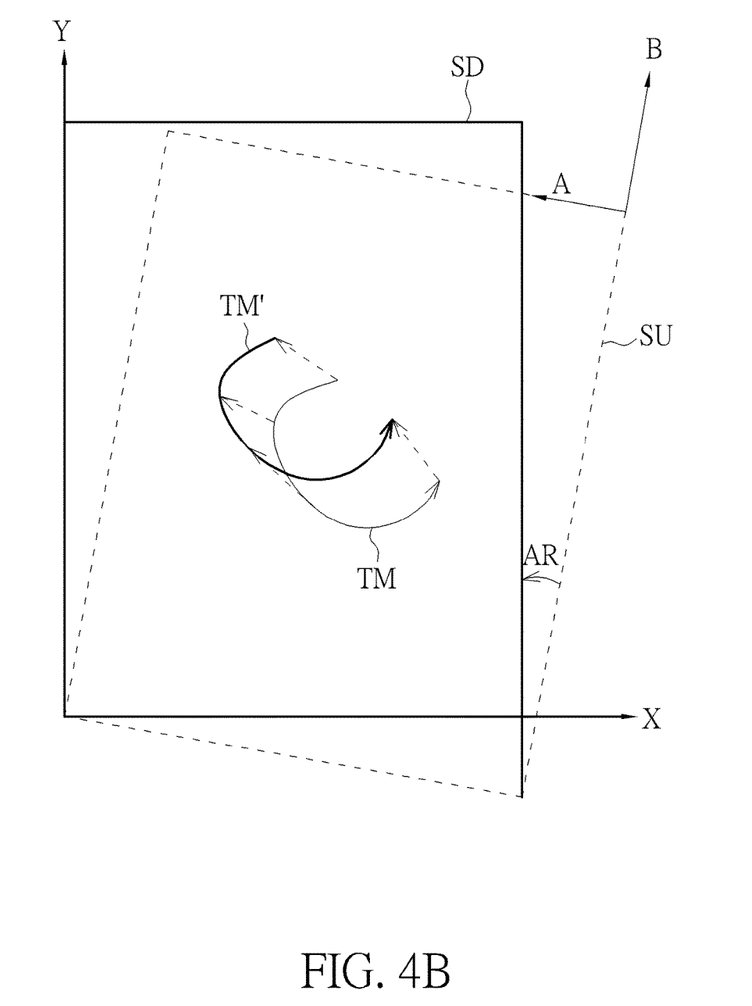
Figure 4C:
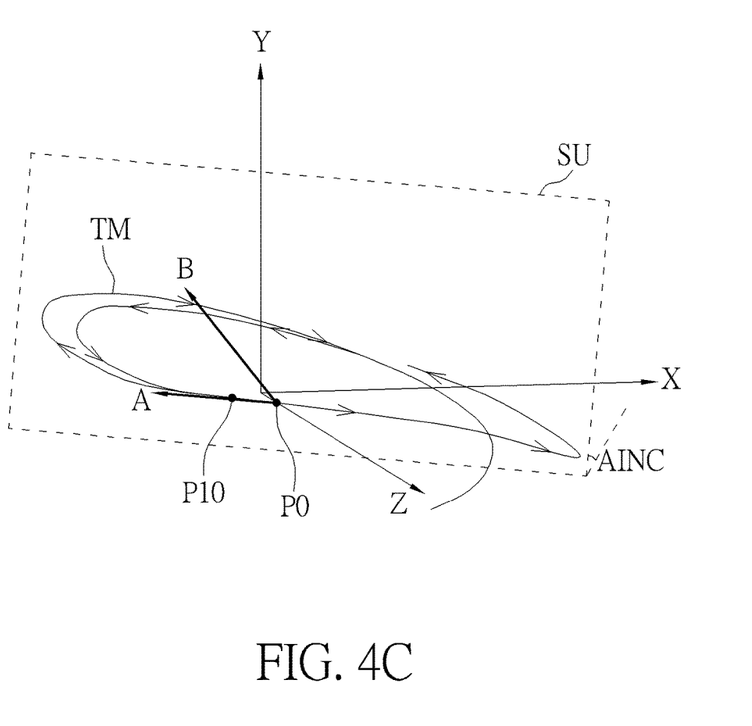

On the other hand, when the second accelerometer 308 is poorly installed and the inclination angle AINC has a significant error, the simulated motion trace TM is difficult to watch, as illustrated in FIG. 4C. With the projection technique of the present invention, the simulated motion trace TM still can be converted into the calibrated trace TM', which is easy for watch. As a result, even though the error of the inclination angle AINC become more and more significant as usage time goes by, the manufacturer and the user no longer have to regularly calibrate positions of the accelerometers since the user can improve athletic skills via the calibration system 30.

Note that, other than the acceleration ACC0, the processing means 314 can choose a vector (P0→P10) formed from the initial point P0 to another point (e.g. the tenth point P10) of the simulated motion trace TM to be the axis vector A according to an alternative embodiment of the present invention.

In addition, computation for the rotational angle AR between the trace surface SU and the display surface SD is known to a skilled person in the art, and is not further narrated herein. As long as the rotational angle AR is acquired, a rotational matrix R of the rotational angle AR is determined, and coordinates of the calibrated trace TM' can be computed via multiplying coordinates of the simulated motion trace TM by the rotational matrix R.

Figure 4D:
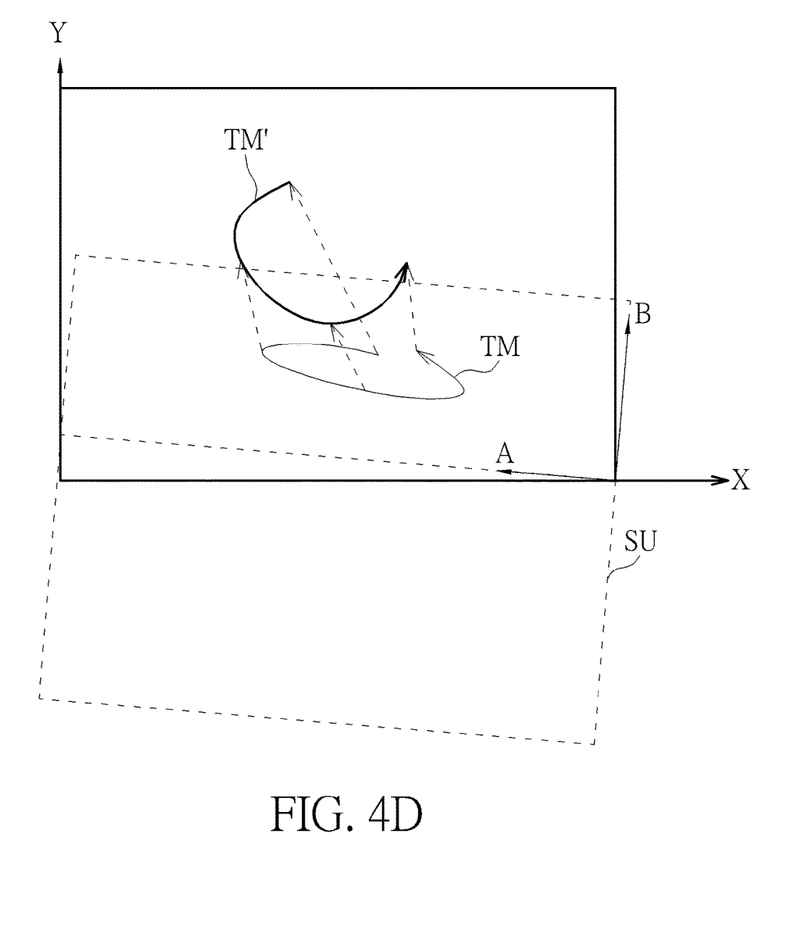

Furthermore, other than the X-Y plane shown FIGS. 4B, 4D, a skilled person in the art can choose a different plane to be the display surface SD based on practical requirements. Alternatively, the user is allowed to adjust the display surface SD to meet individual needs.

To sum up, the present invention is aware that the error of the measured inclination angle cannot be avoided, and directly simulates the motion trace based on the erroneous inclination angle. With vector transformation, the simulated motion trace can be projected and converted into the calibrated trace. As a result, even though the position of the accelerometer is biased due to poor installation or intense usage, the user still can clearly examine the motion trace.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A calibration method for calibrating a simulated motion trace of a sports equipment, the calibration method comprising:

measuring an acceleration, an inclination angle and an azimuth of a terminal of the sports equipment;

computing the simulated motion trace of the terminal according to the acceleration, the inclination angle and the azimuth;

estimating a trace surface on which the simulated motion trace locates according to the simulated motion trace;

computing a rotational angle between the trace surface and a display surface;

projecting the simulated motion trace onto the display surface according to the rotational angle to generate a calibrated trace; and displaying the calibrated trace.

2. The calibration method of claim 1, wherein the step of estimating the trace surface on which the simulated motion trace locates according to the simulated motion trace comprises:

determining a first axis vector and a second axis vector according to the simulated motion trace, wherein an inner product of the first axis vector and the second axis vector is zero.

3. The calibration method of claim 2, wherein the step of determining the first axis vector and the second axis vector according to the simulated motion trace comprises:

choosing an initial acceleration of an initial point of the simulated motion trace to be the first axis vector.

4. The calibration method of claim 3, wherein the step of determining the first axis vector and the second axis vector according to the simulated motion trace further comprises:

selecting a point from the simulated motion trace, such that an inner product of the first axis vector and a vector formed from the initial point to the point is zero; and determining the vector to be the second axis vector.

5. The calibration method of claim 2, wherein the step of determining the first axis vector and the second axis vector according to the simulated motion trace comprises:

choosing a first vector formed from an initial point of the simulated motion trace to a first point of the simulated motion trace to be the first axis vector, wherein the first point is in a neighborhood of the initial point.

6. The calibration method of claim 5, wherein the first point is a tenth point of the simulated motion trace.

7. The calibration method of claim 5, wherein the step of determining the first axis vector and the second axis vector according to the simulated motion trace further comprises:

selecting a second point from the simulated motion trace, such that an inner product of the first axis vector and a second vector formed from the initial point to the second point is zero; and determining the second vector to be the second axis vector.

8. An electronic device for calibrating a simulated motion trace, the electronic device comprising:

a receiving unit, for receiving an acceleration, an inclination angle and an azimuth of a motion;

a storage unit, for storing a program code for executing the following steps:

computing the simulated motion trace of the motion according to the acceleration, the inclination angle and the azimuth;

estimating a trace surface on which the simulated motion trace locates according to the simulated motion trace;

computing a rotational angle between the trace surface and a display surface; and projecting the simulated motion trace onto the display surface according to the rotational angle to generate a calibrated trace; and a display unit, for displaying the calibrated trace.

9. The electronic device of claim 8, wherein the step of estimating the trace surface on which the simulated motion trace locates according to the simulated motion trace comprises:

determining a first axis vector and a second axis vector according to the simulated motion trace, wherein an inner product of the first axis vector and the second axis vector is zero.

10. The electronic device of claim 9, wherein the step of determining the first axis vector and the second axis vector according to the simulated motion trace comprises:

choosing an initial acceleration of an initial point of the simulated motion trace to be the first axis vector.

11. The electronic device of claim 10, wherein the step of determining the first axis vector and the second axis vector according to the simulated motion trace further comprises:

selecting a point from the simulated motion trace, such that an inner product of the first axis vector and a vector formed from the initial point to the point is zero; and determining the vector to be the second axis vector.

12. The electronic device of claim 9, wherein the step of determining the first axis vector and the second axis vector according to the simulated motion trace comprises:

choosing a first vector formed from an initial point of the simulated motion trace to a first point of the simulated motion trace to be the first axis vector, wherein the first point is in a neighborhood of the initial point.

13. The electronic device of claim 12, wherein the first point is a tenth point of the simulated motion trace.

14. The electronic device of claim 12, wherein the step of determining the first axis vector and the second axis vector according to the simulated motion trace further comprises:

selecting a second point from the simulated motion trace, such that an inner product of the first axis vector and a second vector formed from the initial point to the second point is zero; and determining the second vector to be the second axis vector.

* * * * *